US00PP15123P2

(12) United States Plant Patent
Post

(10) Patent No.: US PP15,123 P2
(45) Date of Patent: Aug. 31, 2004

(54) CHRYSANTHEMUM PLANT NAMED 'ORINOCO YELLOW'

(50) Latin Name: *Chrysanthemum×morifolium*
Varietal Denomination: Orinoco Yellow

(75) Inventor: Arie Gerard Post, 's-Gravenzande (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 10/654,564

(22) Filed: Sep. 2, 2003

(51) Int. Cl.[7] ..... A01H 5/00
(52) U.S. Cl. ..... Plt./286
(58) Field of Search ..... Plt./286

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of Chrysanthemum plant named 'Orinoco Yellow', characterized by its daisy type inflorescences with yellow and red purple bi-colored ray and yellow green-colored disc florets; strong and erect flowering stems; early flowering response; good postproduction longevity; and resistance to Chrysanthemum White Rust.

1 Drawing Sheet

Botanical classification/cultivar designation: *Chrysanthemum×morifolium* cultivar Orinoco Yellow.

BACKGROUND OF THE INVENTION

The present invention relates to a new and distinct cultivar of Chrysanthemum plant, botanically known as *Chrysanthemum×morifolium* and referred to by the name 'Orinoco Yellow'.

The new Chrysanthemum is a naturally occurring whole plant mutation of the Chrysanthemum cultivar Orinoco, disclosed in U.S. Plant Pat. No. 14,338. The new Chrysanthemum was discovered and selected by the Inventor on Jan. 10, 2000 within a population of plants of the cultivar Orinoco in a controlled environment in 's Gravenzande, The Netherlands.

Asexual reproduction of the new Chrysanthemum by terminal cuttings in 's Gravenzande, The Netherlands since Feb. 15, 2000, has shown that the unique features of this new Chrysanthemum are stable and reproduced true to type in successive generations.

BRIEF SUMMARY OF THE INVENTION

The cultivar Orinoco Yellow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Orinoco Yellow'. These characteristics in combination distinguish 'Orinoco Yellow' as a new and distinct cultivar:

1. Daisy type inflorescences with yellow and red purple bi-colored ray and yellow green-colored disc florets; typically grown as a spray type.
2. Strong and erect flowering stems.
3. Early flowering response.
4. Good postproduction longevity.
5. Resistant to Chrysanthemum White Rust.

Plants of the new Chrysanthemum differ from plants of the parent, the cultivar Orinoco, primarily in ray floret coloration as plants of the cultivar Orinoco have white and red purple bi-colored ray florets.

Plants of the new Chrysanthemum can be compared to plants of the Chrysanthemum cultivar Yellow Remix, disclosed in U.S. Plant Pat. No. 10,206. In side-by-side comparisons conducted in 's Gravenzande, The Netherlands, plants of the new Chrysanthemum differed from plants of the cultivar Yellow Remix in the following characteristics:

1. Ray floret color of plants of the new Chrysanthemum was lighter yellow and had a stronger contrast than ray floret color of plants of the cultivar Yellow Remix.
2. Spray formation of plants of the new Chrysanthemum was flatter than spray formation of plants of the cultivar Yellow Remix.
3. Plants of the new Chrysanthemum had longer peduncles than plants of the cultivar Yellow Remix.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Orinoco Yellow'.

The photograph at the bottom of the sheet comprises a close-up view of typical leaves and inflorescences of 'Orinoco Yellow'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the spring in 's Gravenzande, The Netherlands, under commercial practice in a glass-covered greenhouse. Plants were initially given long day/short night treatments followed by short day/long night treatments to induce flower initiation and development. During the production of the plants, day temperatures were about 18° C. and night temperatures were about 17° C. Plants were about ten weeks from planting when the photographs and the description were taken.

Botanical classification: *Chrysanthemum×morifolium* cultivar Orinoco Yellow.

Commercial classification: Daisy type Chrysanthemum typically grown as a spray-type cut flower.

Parentage: Naturally occurring whole plant mutation of *Chrysanthemum×morifolium* cultivar Orinoco, disclosed in U.S. Plant Pat. No. 14,338.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous daisy-type cut Chrysanthemum; typically grown as a spray type; erect and strong flowering stems.

*Growth rate.*—Moderate; moderately vigorous.

*Flowering stem description.*—Length: About 80 cm. Diameter, at apex: About 6 mm. Strength: Strong. Aspect: Erect. Branching habit: Plants are typically grown as single stems. Color: 144A.

*Foliage description.*—Arrangement: Alternate. Length: About 13.5 to 14.5 cm. Width: About 10 cm. Apex: Mucronate. Base: Attenuate. Margin: Pinnately lobed. Texture: Rough; both surfaces pubescent. Petiole length: About 2.5 to 3 cm. Petiole diameter: About 2 to 3 mm. Color: Developing foliage, upper surface: 139A. Developing foliage, lower surface: 137B. Fully expanded foliage, upper surface: 137A. Fully expanded foliage, lower surface; 147B. Venation, upper and lower surfaces: 146C. Petiole, upper and lower surfaces: 146C.

Inflorescence description:

*Appearance.*—Daisy type inflorescence form with elongated oblong-shaped ray florets. Inflorescences borne on terminals above foliage. Disk and ray florets develop acropetally on a capitulum. Not fragrant. Typically grown as a spray type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 48 to 49 days later.

*Postproduction longevity.*—Inflorescences will maintain good substance and form for about 3.5 weeks after harvesting.

*Quantity of inflorescences per flowering stem.*—About 17 inflorescences per flowering stem.

*Inflorescence size.*—Diameter: About 7.5 cm. Depth (height): About 2 cm. Diameter of disc: About 1.5 cm.

*Inflorescence buds.*—Length: About 6 mm. Diameter: About 8 mm. Shape: Oblate. Color: 137C.

*Ray florets.*—Length, fully developed: About 3.4 cm. Width, fully developed: About 1.3 cm. Shape: Elongate oblong to somewhat spatulate. Apex: Rounded. Base: Fused; obtuse. Margin: Entire. Texture: Smooth, glabrous. Number of ray florets per inflorescence: About 27 to 40. Color: When opening, upper and lower surfaces: Towards the apex, 10A; towards the base, 187A. Fully opened, upper surface: Towards the apex, 8B; towards the base, 59A. Fully opened, lower surface: Towards the apex, 8B; towards the base, 61A.

*Disc florets.*—Shape: Tubular. Length: About 5 mm. Width: About 1 mm. Number of disc florets per inflorescence: About 164. Color: Immature: 145C. Mature: 144D.

*Peduncles.*—Length, terminal peduncle: About 6 cm. Length, fourth peduncle: About 8 cm. Diameter: About 2 mm. Angle: About 45° from vertical. Texture: Pubescent. Color: 148A.

*Reproductive organs.*—Androecium: Present on disc florets only. Anther color: 14A. Pollen color: 14A. Gynoecium: Present on both ray and disc florets.

*Seed/fruit.*—Seed and fruit production has not been observed.

Disease/pest resistance: Plants of the new Chrysanthemum have been observed to be resistant to Chrysanthemum White Rust. Plants of the new Chrysanthemum have not been observed to be resistant to other known pathogens and pests common to Chrysanthemum.

It is claimed:

1. A new and distinct cultivar of Chrysanthemum plant named 'Orinoco Yellow', as illustrated and described.

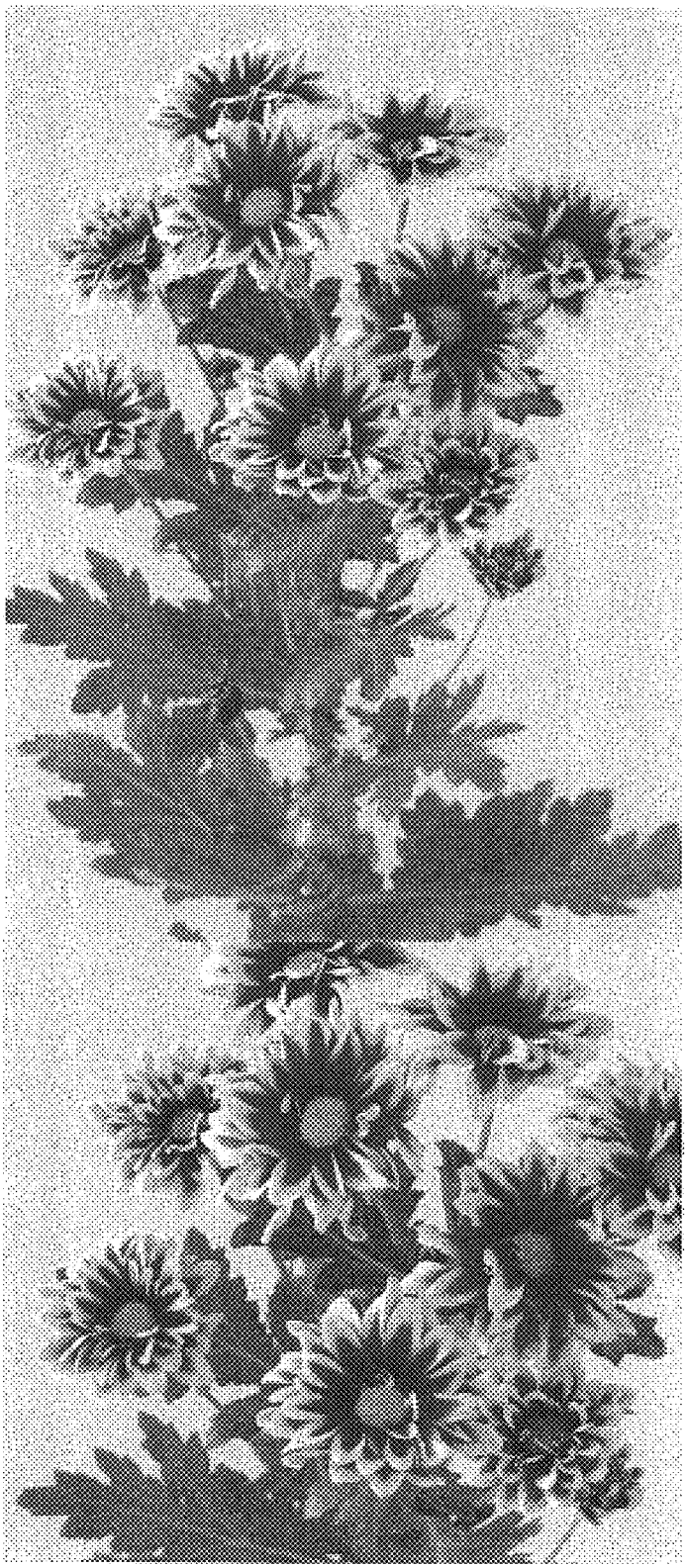

* * * * *